(12) United States Patent
Blay et al.

(10) Patent No.: US 12,023,514 B2
(45) Date of Patent: Jul. 2, 2024

(54) DISPOSABLE FLEXIBLE ELECTRONIC PHOTOTHERAPY DEVICE

(71) Applicant: M3 HEALTH INDÚSTRIA E COMÉRCIO DE PRODUTOS MÉDICOS, ODONTOLÓGICOS E CORRELATOS S.A., Jundiai (BR)

(72) Inventors: Alberto Blay, São Paulo (BR); Marcus Vinicius Lucas Ferreira, Belo Horizonte (BR)

(73) Assignee: M3 HEALTH INDÚSTRIA E COMÉRCIO DE PRODUTOS MÉDICOS, ODONTOLÓGICOS E CORRELATOS S.A., Jundiai (BR)

( * ) Notice: Subject to any disclaimer, the term of this patent is extended or adjusted under 35 U.S.C. 154(b) by 544 days.

(21) Appl. No.: 17/286,286

(22) PCT Filed: Oct. 16, 2019

(86) PCT No.: PCT/BR2019/050445
§ 371 (c)(1),
(2) Date: Apr. 16, 2021

(87) PCT Pub. No.: WO2020/077427
PCT Pub. Date: Apr. 23, 2020

(65) Prior Publication Data
US 2021/0402207 A1 Dec. 30, 2021

(30) Foreign Application Priority Data
Oct. 16, 2018 (BR) .................. 10 2018 071305 1

(51) Int. Cl.
*A61N 5/06* (2006.01)
*A61N 5/067* (2006.01)

(52) U.S. Cl.
CPC ........... *A61N 5/0616* (2013.01); *A61N 5/067* (2021.08); *A61N 2005/0645* (2013.01); *A61N 2005/0652* (2013.01); *A61N 2005/0653* (2013.01)

(58) Field of Classification Search
CPC .... A61N 2005/0626; A61N 2005/0645; A61N 2005/0652; A61N 2005/0653; A61N 5/0616; A61N 5/067
See application file for complete search history.

(56) References Cited

U.S. PATENT DOCUMENTS

2006/0217787 A1* 9/2006 Olson .................. A61N 5/0616
607/88
2008/0275327 A1 11/2008 Faarbaek et al.
2010/0253225 A1 10/2010 Lifka et al.

FOREIGN PATENT DOCUMENTS

KR 101031950 4/2011

OTHER PUBLICATIONS

International Preliminary Report on Patentability dated Jan. 15, 2020 in International Application No. PCT/BR2019/050445.
(Continued)

*Primary Examiner* — Amanda K Hulbert
(74) *Attorney, Agent, or Firm* — B. Aaron Schulman, Esq.; Stites & Harbison, PLLC (57) ABSTRACT

A disposable and flexible electronic device for photobiomodulation of biological tissues, particularly applied as a bandage in several formats, in either domestic or clinical applications, biostimulating or biomodulating biological tissues, for healing wounds and treating inflammation, edema and pain.

13 Claims, 4 Drawing Sheets

(56) References Cited

OTHER PUBLICATIONS

International Search Report dated Jan. 15, 2020 in International Application No. PCT/BR2019/050445.
Written Opinion dated Jan. 15, 2020 in International Application No. PCT/BR2019/050445.

* cited by examiner

DISPOSABLE FLEXIBLE ELECTRONIC PHOTOTHERAPY DEVICE

FIELD OF THE INVENTION

The present invention relates to an electronic light emitting device indicated particularly for use as a bandage in several formats. This device is flexible and serves for domestic or clinical use and is intended for biostimulation or biomodulation of biological tissues where there is inflammation, edema and pain.

Such a device can be self-applied, self-adhesive, single-use, that is, disposable for home use without the need for external control. The original characteristics of this electronic device allow to use phototherapy in a portable way by means of LEDs (Light Emitting Diode) or OLEDs (Organic Light Emitting Diode) embedded in the referred device, emitting in the wavelength in the range of red and/or infrared to heal wounds, decrease local pain, decrease local inflammation and also, decrease edema.

BACKGROUND OF THE INVENTION

Low-Level Laser (Light) Therapy (LLLT) phototherapy is an increasing technology on the world stage. LLLT has entered the arsenal of modern medicine as an efficient component to assist in the treatment for rejuvenation and skin diseases, mainly because it applies non-invasive therapies. This therapy was discovered in the late 1960s, but only recently has it been widely applied in medicine, dentistry, physiotherapy and veterinary medicine. There are several studies showing a wide range of applications for use in dermatology, especially in indications where stimulation of healing is required, reduction of inflammation, reduction of cell death and skin rejuvenation. The application of LLLT to pigmentation disorders can work in both directions, producing vitiligo repigmentation and depigmentation of hyperpigmented lesions, depending on dosimetric parameters. However, there is still a credibility gap that needs to be bridged before LLLT is routinely applied by dermatologists or even for home use. This scenario begins to change with the introduction of devices based on an LED matrix, as it simplified the application in large areas of the skin, and mainly by reducing many of the concerns previously associated with lasers, such as safety, the need for trained personnel to operate them and costs. [source: Avci P, Gupta A, Sadasivam M, et al. Low-level laser (light) therapy (LLLT) in skin: stimulating, healing, restoring. Seminars in cutaneous medicine and surgery. 2013; 32 (1): 41-52.]

Today's phototherapy devices and technologies dedicated to photobiomodulation of biological tissues do not simultaneously have the following characteristics: domestic use, flexible, fully portable, single-use, self-adhesive, disposable, and because light sources do not require external control and are activated when placing the bandage on the surface of the biological tissue. There is, therefore, a technological gap for the use of phototherapy for wound healing by means of flexible single-use light-emitting bandages that can be used to protect a wound and at the same time accelerate the healing process.

There are some devices in the national and international market in order to perform phototherapy for wound healing. The vast majority of these devices are rigid structures and use controlled by a large equipment that can be connected to the mains, or operated by rechargeable batteries, such as the developments described in the patent documents: MU 8303493-5, MU 8301504-5, U.S. Pat. No. 7,198,633, US 2009/0296384, WO 2004/075984, JP 75009391, BR 0705193-0, BR 0406340-6, U.S. Pat. No. 5,766,233, RU 2232610 and CA 2363383.

Patent document MU 8303493-5 describes an equipment for biomodulation of epithelial, bone and muscle tissue consisting of red and/or infrared LEDs. The present invention differs from this equipment due to the fact that it uses wavelengths in the range of red and infrared, it is for single use, totally flexible, self-adhesive, disposable and because the light sources are activated when placing the bandage on the surface of biological tissue.

Patent document MU 8301504-5 discloses an equipment for biostimulation of oral tissues by means of red and/or infrared LEDs. The equipment has the form of a mask that fits the patient's face. The present invention is not anticipated by this document since it uses wavelengths in the range of red and infrared, it is for single use, totally flexible, self-adhesive, disposable and because the light sources are activated when placing the bandage on the surface of the biological tissue.

U.S. Pat. No. 7,198,633, on the other hand, describes a phototherapy equipment consisting of a light chamber with an internal reflecting surface, formed by a set of LEDs that emit different wavelengths. An electronic circuit is used to connect one or more LEDs to produce different wavelengths. The present invention differs from this equipment due to the fact that it is for single use, totally flexible, self-adhesive, disposable and because the light sources are activated when placing the bandage on the surface of the biological tissue.

In addition, document US 2009/0296384 relates to a phototherapy device that comprises at least one light emitter emitting in the range 600-630 nm. The present invention differs from this device due to the fact that it is for single use, totally flexible, self-adhesive, disposable and because the light sources are activated when placing the bandage on the surface of the biological tissue.

Patent document WO 2004/075984 refers to a technique to promote wound healing by means of polychromatic radiation in the wavelength range that includes the visible spectrum and the near infrared (405-904 nm). This document reveals a method of treatment, not mentioning any type of device. The present invention uses only a wavelength in the range of red and infrared, it is for single use, totally flexible, self-adhesive, disposable and the light sources are activated when placing the bandage on the surface of the biological tissue.

In addition, the patent document JP 75009391 discloses a device comprising an infrared light emitting diode and a system that converts infrared rays into red light by means of a fluorescence system. The present invention differs from this device due to the fact that it uses wavelengths in the range of red and infrared, is single-use, totally flexible, self-adhesive, disposable and because the light sources are activated when placing the bandage on the surface of biological tissue.

Patent document BR 0705193-0 refers to a device for foot therapy composed of an infrared LED and a red LED. The present invention differs from this device due to the fact that it uses wavelengths in the range of red and infrared, is single-use, totally flexible, self-adhesive, disposable and because the light sources are activated when placing the bandage on the surface of biological tissue.

Patent document BR 0406340-6 discloses equipment with a red or infrared LED for therapeutic use. The present invention differs from this equipment due to the fact that it uses wavelengths in the range of red and infrared, it is for single use, totally flexible, self-adhesive and because the light sources are activated when placing the bandage on the surface of biological tissue.

Document U.S. Pat. No. 5,766,233 describes a device consisting of light-emitting diodes for wound healing. The device emits infrared light and then red light. The present invention differs from this device due to the fact that it uses wavelengths in the range of red and infrared, is single-use, totally flexible, self-adhesive, disposable and because the light sources are activated when placing the bandage on the surface of biological tissue.

Patent document RU 2232610 discloses a device consisting of 15 LEDs for application in physiotherapy. The device can emit in the red wavelength and also in the infrared. The present invention differs from this device due to the fact that it uses wavelengths in the range of red and infrared, is single-use, totally flexible, self-adhesive, disposable and because the light sources are activated when placing the bandage on the surface of biological tissue.

In addition, the patent document CA 2 363 383 describes a device that uses red and infrared wavelengths for photodynamic stimulation of human tissue cells. The present invention differs from this document due to the fact that it uses wavelengths in the range of red and infrared, it is for single use, totally flexible, self-adhesive, disposable and because the light sources are activated when the bandage is applied on the surface of biological tissue.

There are several applications with flexible devices for the healing of skin wounds, consisting of light sources of the LASER, LED and/or OLED type, of different wavelengths, embedded in moldable substrates to the treatment area, with different shapes and sizes, such as example, the developments described in the following documents: BR202012033571-4; US2010/0179469; US2010/0253225; BR0707477-8; US2004/0166146; US2005/0177093; US2006/0167532; US2006/0217690; US2007/0233208; US2007/0208395; US2007/0239232; US2008/0269849; US2010/0256541; WO01/54770; WO2006/101735; WO2009/103165; WO2010/064035; GB2360460; US2002/0029071; US2009/0163819.

Patent document BR 20 2012 033571-4 discloses a flexible device using red and infrared LEDs or OLEDs, which are coupled to a control unit that is connected to the mains. The present invention differs from this device due to the fact that it uses wavelengths in the range of red and infrared, it is for single-use, totally flexible, self-adhesive, disposable and because the light sources are activated when placing the bandage on the surface of biological tissue.

US patent document 2010/0179469 describes a device consisting of a flexible, transparent OLED substrate, printed on a textile or non-textile material. Emits visible radiation up to the near infrared, with control of the parameters of the luminous radiation. In addition, it allows activation and deactivation of at least a part of the OLEDs. The present invention differs from this device due to the fact that it uses wavelengths in the range of red and infrared, it is for single-use, totally flexible, self-adhesive, disposable and because the light sources are activated when placing the bandage on the surface of biological tissue.

The patent document US 2010/0253225 discloses an OLED system on a flexible substrate that can be a synthetic resin, glass, metal or textile, made in the form of bandages or clothing adaptable to the treatment region. It comprises intensity and temperature control. The present invention differs from this system due to the fact that it uses wavelengths in the range of red and infrared, it is for single-use, totally flexible, self-adhesive, disposable and because the light sources are activated when placing the bandage on the surface of biological tissue.

In addition, the patent document BR 0707477-8 refers to a flexible device for LEDs and/or OLEDs featuring a substrate of textile or non-textile material, as well as wavelength and intensity adjustment settings. This device emits at least one wavelength between 440 nm and 480 nm. The present invention differs from this device due to the fact that it uses wavelengths in the range of red and infrared, it is for single-use, totally flexible, self-adhesive, disposable and because the light sources are activated when placing the bandage on the surface of biological tissue.

Patent document US 2004/0166146 deals with a continuous use phototherapy bandage, capable of emitting radiation to a specific area, for the treatment of wounds. The bandage emits visible and near-infrared radiation. The present invention differs from this bandage in that it uses wavelengths in the red and infrared range, is single-use, fully flexible, self-adhesive, disposable and because the light sources are activated when placing the bandage on the surface of biological tissue.

Patent documents US 2005/0177093 and US 2010/0256541 refer to flexible devices for phototherapy indicated for the reduction of inflammation and pain, besides wound healing. The device has layers of LEDs connected to optical fibers, which emit light radiation in the spectral range from ultraviolet to near infrared. The present invention differs from these devices due to the fact that it uses wavelengths in the red and infrared range, it is for single-use, totally flexible, self-adhesive, disposable and because the light sources are activated when placing the bandage on the surface of biological tissue.

Patent document US 2006/0167532 discloses an arrangement of LEDs or OLEDs tied to a flexible substrate with radiation emission at various wavelengths. The substrate can have various shapes and sizes and can be inserted in a transparent polymer or in a fabric mesh, allowing it to be molded to the treatment area. The present invention differs from this arrangement due to the fact that it uses wavelengths in the range of red and infrared, it is for single-use, totally flexible, self-adhesive, disposable and because the light sources are activated when placing the bandage on the surface of biological tissue.

Patent document US 2006/0217690 discloses a device for treatment of skin lesions, formed by a set of light emitters that can be a LASER, an LED or OLED. The emitters are arranged in a flexible tissue mesh, which can be a polymer, foam, metal and the like, so that it can adapt to the treatment region. The device has controls for light radiation parameters as well as local temperature. The present invention differs from this device due to the fact that it uses wavelengths in the range of red and infrared, it is for single-use, totally flexible, self-adhesive, disposable and because the light sources are activated when placing the bandage on the surface of biological tissue.

In addition, patent document US 2007/0233208 deals with a flexible phototherapeutic bandage that emits red and infrared light. The present invention differs from this bandage due to the fact that it uses wavelengths in the red and infrared range, it is for single-use, totally flexible, self-adhesive, disposable and because the light sources are activated when placing the bandage on the surface of biological tissue.

Patent document US 2007/0208395 discloses flexible LASER and/or LED substrates with a wide spectral range (200-2000 nm) and external control of treatment parameters.

The substrates can consist of fabric, rubber, elastomer or thermoplastic, they are adaptable to the treatment area and can be made in different shapes and sizes. The present invention differs from these substrates due to the fact that it uses wavelengths in the red and infrared range, it is for single-use, totally flexible, self-adhesive, disposable and because the light sources are activated when placing the bandage on the surface of biological tissue.

Patent document US 2007/0239232 discloses a phototherapy device emitting red and infrared light indicated for the treatment of wounds. The equipment is based on a flexible optical substrate consisting of a light source with one or more light emitters. The present invention differs from this device due to the fact that it uses wavelengths in the range of red and infrared, it is for single-use, totally flexible, self-adhesive, disposable and because the light sources are activated when placing the bandage on the surface of biological tissue.

Patent document US 2008/0269849 discloses a phototherapy device that simultaneously emits two wavelengths that can comprise the spectral range of red and infrared. The present invention differs from this device due to the fact that it uses wavelengths in the range of red and infrared, it is for single-use, totally flexible, self-adhesive, disposable and because the light sources are activated when placing the bandage on the surface of biological tissue.

Patent document WO 01/54770 describes a phototherapy device emitting visible and/or infrared radiation (400-2000 nm) for the treatment of irregular surfaces. It has external control that modulates the parameters of light radiation and allows the activation and deactivation of at least a part of the diodes. The present invention differs from this device due to the fact that it uses wavelengths in the range of red and infrared, it is for single-use, totally flexible, self-adhesive, disposable and because the light sources are activated when placing the bandage on the surface of biological tissue.

Patent document WO 2006/101735, on the other hand, discloses a phototherapy device emitting red or infrared radiation for treatment of wounds. It has a flexible optical substrate consisting of a light source with one or more light emitters and can be configured to emit light to one or more areas of the body. The present invention differs from this device due to the fact that it uses wavelengths in the range of red and infrared, it is for single-use, totally flexible, self-adhesive, disposable and because the light sources are activated when placing the bandage on the surface of biological tissue.

Patent document WO 2009/103165 describes a phototherapy device with several light sources (red and/or infrared) arranged to emit radiation at the periphery of an injury. The present invention differs from this document due to the fact that it uses wavelengths in the range of red and infrared, it is for single-use, totally flexible, self-adhesive, disposable and because the light sources are activated when placing the bandage on the surface of biological tissue.

In addition, patent documents WO 2010/064035, US 2002/0029071 and GB 2 360 460 refer to devices emitting wavelengths in the red range capable of adapting to irregular body surfaces. The present invention differs from these devices due to the fact that it uses wavelengths in the red and infrared range, it is for single-use, totally flexible, self-adhesive, disposable and because the light sources are activated when placing the bandage on the surface of biological tissue.

Patent document US 2009/0163819 describes a phototherapy device emitting red and infrared wavelengths consisting of at least one LED and/or OLED capable of adapting to irregular body surfaces. The present invention differs from this device due to the fact that it uses wavelengths in the range of red and infrared, it is for single-use, totally flexible, self-adhesive, disposable and because the light sources are activated when placing the bandage on the surface of biological tissue.

Therefore, in the state of the art, there is no equivalent solution to the presented here in the present invention that combines technical differentials, economic advantages, safety and reliability.

Objectives of the Invention

Thus, it is an objective of the present invention to provide a solution to the inconveniences generated by the use of LLLT technology devices available on the market, which are mostly large with external control.

It is another objective of the present invention to provide a device being particularly a disposable bandage with flexible electronic devices embedded without the need for an external controller, being self-applied, portable and drastically reducing the cost to the end user compared to techniques and devices available on the market.

It is another objective of the present invention to provide a phototherapy device as a bandage for photobiomodulation of biological tissues, consisting of a biocompatible adhesive microporous tape and on this is located the light emitting unit connected to a flexible battery.

It is another objective of the present invention to provide a phototherapy device that comprises a circuit driven through a mechanical contact, normally closed, which is initially isolated by a substrate and which must be removed manually after said device is placed in the desired region, giving start the current flow from the battery to activate the light emitting unit.

In addition, it is another objective of the present invention to provide a phototherapy device that emits light in the wavelength range of red and infrared.

Furthermore, it is another objective of the present invention to provide a single use phototherapy device, totally flexible, self-adhesive, disposable.

In addition, it is another objective of the present invention to provide a phototherapy device in which the light sources are activated at the moment of placing the bandage on the surface of the biological tissue.

It is also another objective of the present invention to provide a phototherapy device particularly indicated to be used as a bandage in several formats.

It is also another objective of the present invention to provide a phototherapy device for home or clinical use.

In addition, it is another objective of the present invention to provide a phototherapy device indicated for biostimulation or biomodulation of biological tissues where there is inflammation, edema and pain.

Furthermore, it is another objective of the present invention to provide a phototherapy device indicated to heal wounds, decrease local pain, modulate local inflammation and also, reduce edema.

In addition, it is another of the objectives of the present invention to provide a phototherapy device indicated to act together photoabsorbers in the range of 630 to 910 nm to perform photodynamic therapy.

SUMMARY OF THE INVENTION

The present invention achieves these and other objectives by means of a device particularly indicated for use as a bandage for phototherapy that comprises:

a biocompatible adhesive microporous tape forming a support base for the flexible phototherapy device;

a flexible light emitting unit, composed of an arrangement of LEDs or OLEDs connected to a primary flexible battery by means of a flexible printed circuit and the light emitters emit wavelengths in the red range between 530 to 700 nm and infrared between 700 nm a 910 nm;

at least a portion of the device being superimposed on a target area in a patient; and at least this portion being able to conform to a surface area of the target area.

BRIEF DESCRIPTION OF THE DRAWINGS

The present invention will be described based on the drawings attached here, which illustrate.

DETAILED DESCRIPTION OF THE INVENTION

As can be seen below, the present invention relates to a device particularly indicated for use as a bandage for phototherapy comprising:

a biocompatible adhesive microporous tape 1 forming a support base for the flexible phototherapy device;

a flexible light emitting unit 2, composed of an arrangement of LEDs or OLEDs 3 connected to a primary flexible battery 4 by means of a flexible printed circuit 5, with light emitters emitting wavelengths in the red range between 530 to 700 nm and infrared between 700 nm to 910 nm;

at least a portion of the device being superimposed on a target area in a patient; and at least this portion being able to conform to a surface area of the target area.

In the teachings of the state of the art, the usual is to find flexible light emitters that are not self-adhesive, disposable and for personal and unique use (home use). These emitters are usually operated by an external controller, either wired or wirelessly. Also, with regard to wearable devices, they will always have a system to control the light source.

Thus, the present invention is unique when it comes to a single-use phototherapy bandage. Its main and differential features are the flexible battery and the flexible printed circuit. It is, therefore, a flexible, disposable, self-adhesive bandage, without a controller, "pre-set".

In the preferred embodiments, the flexible printed circuit 5 is miniaturized. In addition, the material used in the microporous tape is absorbable or non-absorbable synthetic polymer.

Figure 2:
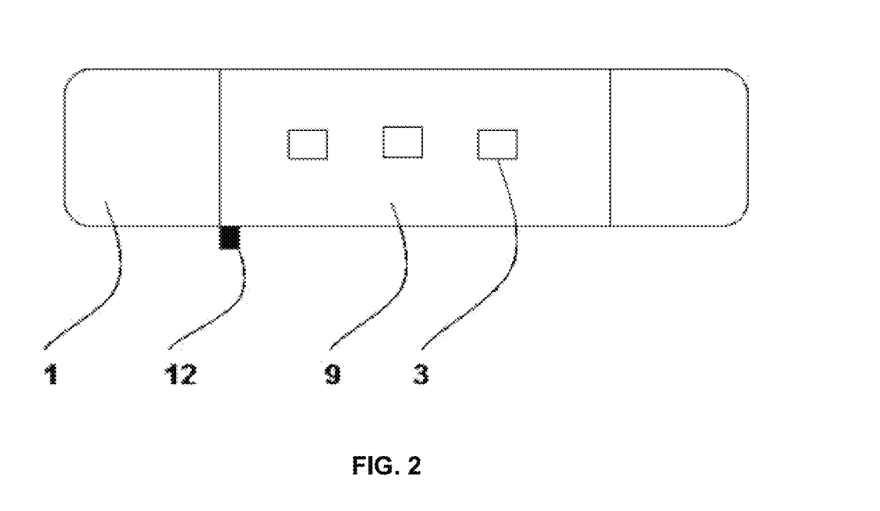
FIG. 2 illustrates the front view of the device object of the present invention.
Figure 3:
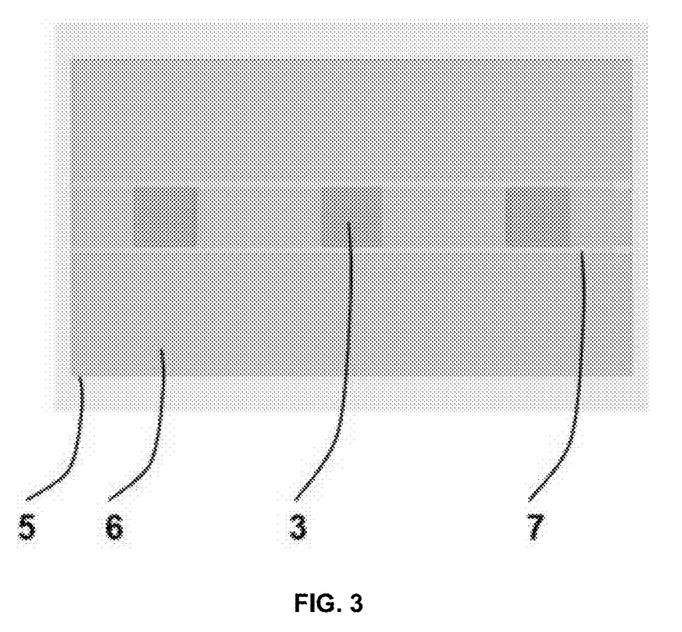
FIG. 3 illustrates the printed circuit comprised in the device object of the present invention.

In addition, the present invention is understood as a bandage for photobiomodulation of biological tissues that comprises a structure being a biocompatible adhesive microporous tape 1 as illustrated in FIG. 2. On this structure 1 is located a light emitting unit 2 composed preferably of an arrangement of LEDs or OLEDs 3 that can vary in number according to the size and shape of the bandage, without restrictions on the number of light sources or the shape of the bandage. The LEDs or OLEDs 3 are connected to a primary flexible battery 4, shown in FIG. 4, through a flexible printed circuit 5, shown in FIG. 3, making it a flexible electronic device.

Figure 4:
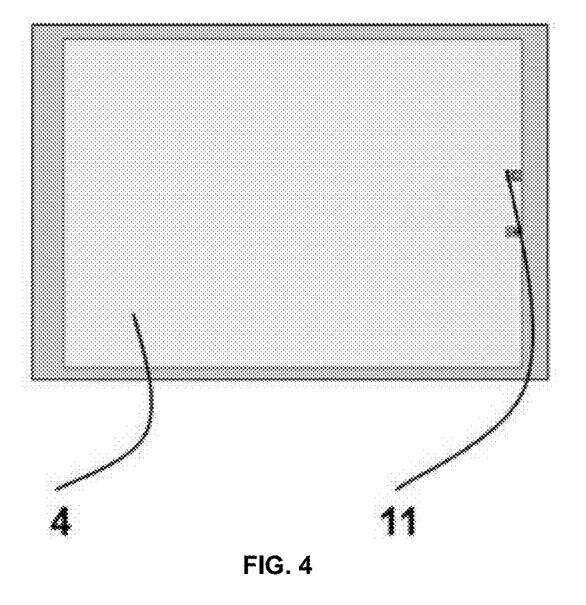
FIG. 4 illustrates battery and spring comprised in the device object of the present invention.

In preferred embodiments, the present invention comprises battery 4 being flexible, ultra-thin and solid-state lithium polymer batteries, which do not combust even when punctured, twisted or heated, as they do not contain volatile liquids thus eliminating the potential for combustion. Furthermore, such flexible batteries allow customization, which is not possible with other models such as ordinary lithium batteries. This makes them ideal for medical applications and products, as today's devices and applications require powerful, small, flexible and safe sources of energy.

Also, in preferred embodiments, the printed circuit 5 is a microchip that pulsates the light from the LEDs at 300 Hz.

Regarding the LED or OLEDs 3 arrangements, the possibilities are diverse; it is possible, for example, the device of the present invention comprise 1 point LED, or 3 LEDs or even 9 LEDs for large areas, depending on the application, the size of the area, the need for light emission.

The flexible printed circuit 5 is a technology used in the manufacture of electronic circuits through the assembly of electronic devices on flexible polymeric substrates, such as polyimide (Kapton), polyethylene terephthalate (PET) or any flexible polymeric film, without restrictions. The assembly of flexible electronics can be done using components identical to those used on rigid circuit boards, making it possible to shape the boards into a desired shape, or even remain flexible during use. These flexible printed circuits can be made with photolithographic technology, lamination or printed electronics, without restrictions on the method of manufacturing the flexible printed circuit.

Figure 6:
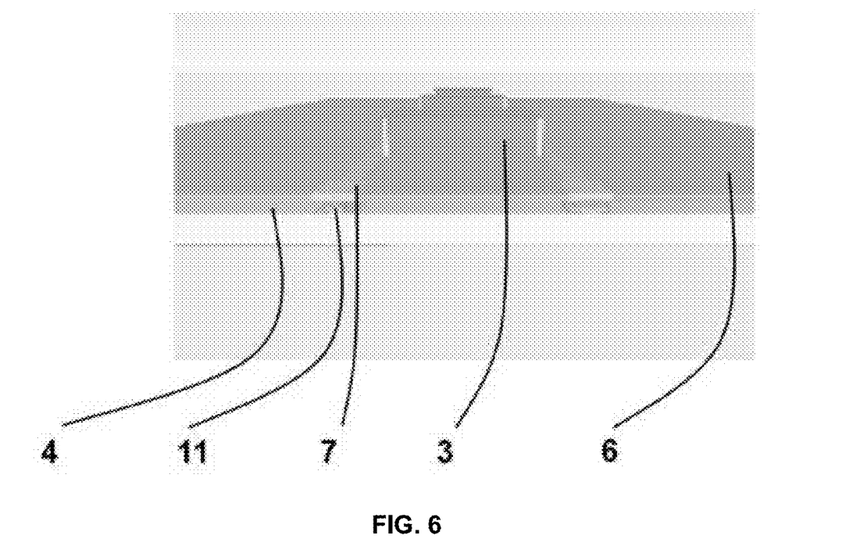
FIG. 6 represents a side view of the printed circuit with fixed components comprised in the device object of the present invention.

The flexible printed circuit 5 of the device object of the present invention, illustrated in FIG. 6, is composed of a substrate 6 with tracks 7, which represent the wires for electrical connections between the components, the tracks were manufactured by silver inkjet printing on a polyimide track 6 without restrictions for the substrate printing process, which reduces material waste compared to traditional manufacturing methods. It is noteworthy that the track 7 is the electrical conductor deposited on the substrate, forming the printed circuit board, which, in the present invention, is flexible.

The fixation of the arrangement of LEDs 3 and battery 4 on the printed circuit 5 is carried out by conductive glue, conductive epoxy or solder, without restrictions. The connection between battery 4 and the arrangement of LEDs 3 is made through a track 7 of the printed circuit that connects the positive and negative poles of battery 4 and between the cathode and anode of the arrangement of LEDs 3. The primary flexible battery 4 has a direct connection to the arrangement of LEDs 3, connected in parallel and/or series, without restrictions on the architecture of the emitters.

The circuit 5, the structure 1, the battery 4 and the arrangement of LEDs or OLEDs 3 are encapsulated in a layer of polyimide 8, without restriction as to the type of material, to guarantee the hygiene of the device object of the present invention and the safety of the possible electrical hazards, the light-emitting unit.

There is also an inner layer 9, composed of a microporous tape positioned in the center of the structure 1 in which the arrangement of LEDs 3 is located. In layer 1 and inner layer 9 they are formed by a microporous adhesive in order to guarantee comfort, sweating and fixation to the injured skin, without restriction.

The device of the present invention is capable of being sterilized.

Device Activation

Figure 1:
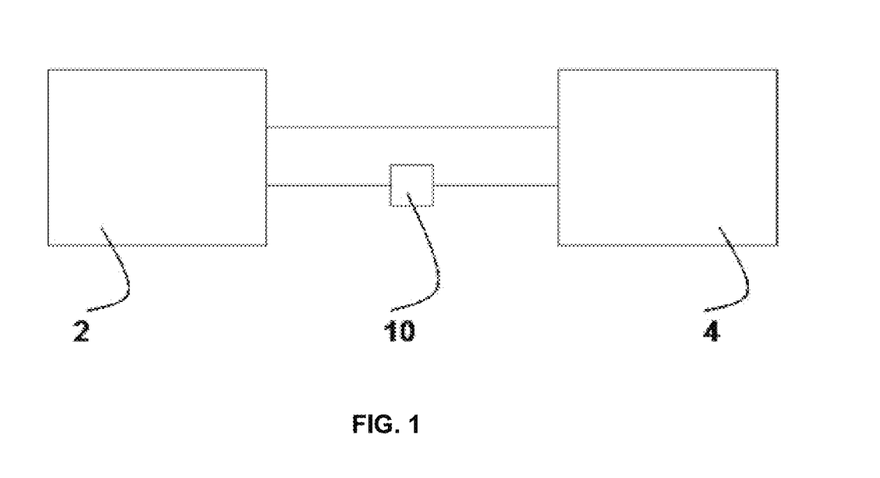
FIG. 1 represents the block diagram of the device object of the present invention.
Figure 5:
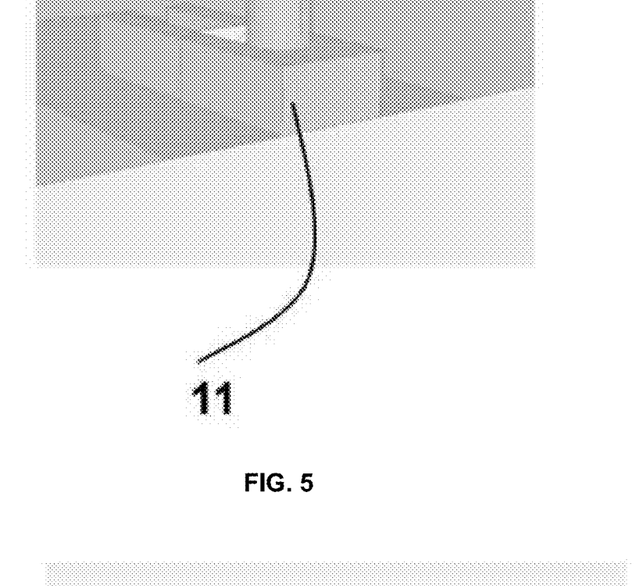
FIG. 5 represents a spring attached to the battery comprised in the device object of the present invention.

The electrical circuit is initially open, isolated by a dielectric tape 12, and the electrical contact is made by mechanical activation 10 by means of a spring 11, illustrated in FIG. 5, fixed on the printed circuit line or on the battery bus 4. After the removal of the tape 12, the spring 11 closes the electrical circuit lighting the light emitting unit 2 and the phototherapy process begins. The mechanical activation is illustrated in FIG. 1.

To drive the device object of the present invention, it is necessary to remove the protective tape 12, this process being irreversible. This device differs from other available technologies in that it does not need an external controller, either connected to the mains or to some rechargeable battery system.

Figure 7:
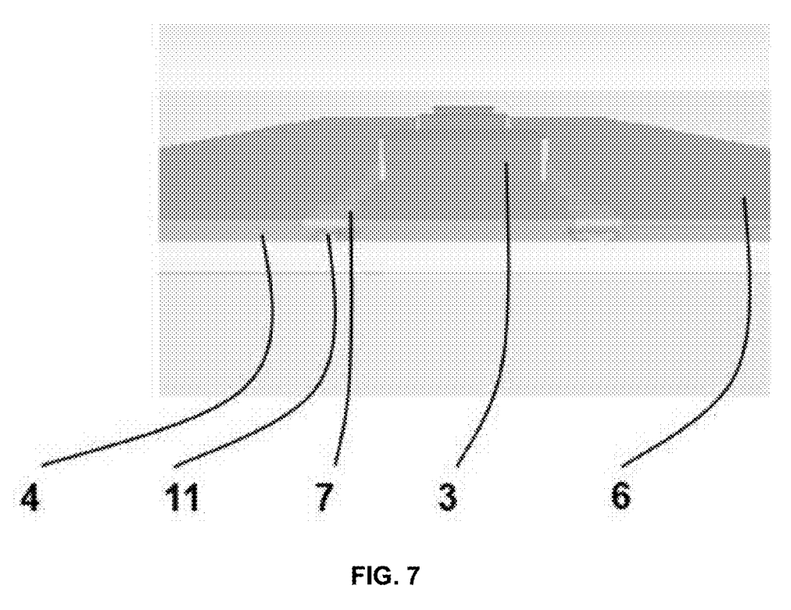
FIG. 7 represents a side view of the device object of the present invention with separate components.

Preferably, the device object of the present invention, illustrated in FIG. 7, has a thickness of 0.4 cm, without restrictions, so as not to interfere with its mechanical flexibility.

The light emitting unit 2 preferably uses 1 or 2 types of LEDs or OLEDS 3 that emit a frequency of molecular excitation within the red light spectrum between 630 to 700 nm and infrared between 700 to 910 nm, with radiated energy from 1 to 4 J/cm2, without restrictions, lasting from 1 to 5 minutes, without restrictions, these pre-established parameters being necessary for the operation of low-intensity phototherapy. Once the device is used, it extinguishes the battery charge 4 and cannot be activated again and must be discarded.

Said device in an alternative embodiment may have a controller with timer (not illustrated) for activating the light emitting unit 2. With the controller, it will be possible to perform the pulsed activation of the arrangement of LED 3 at different frequencies. The controller can activate different types of LEDs 3 and/or activate LEDs 3 at pre-established time intervals in order to carry out more than one therapy assignment by controlling the use of battery energy 4.

In an ideal scenario, the emitter system 2 would be formed by a flexible, thin and flat lamp covering the entire surface of the device in contact with the lesion. The device, if manufactured in a continuous production process, in which the entire electronic part can be manufactured using low-cost printing and/or coating techniques, makes the final cost of the device very low.

The present invention has numerous technical and economic advantages when compared to the state of the art, some of which are listed below:

The device object of the present invention is characterized by acting in a non-invasive way, in contact or close to the wounds, and can be made in sizes according to the area of the wound;

The device is portable, has easy application and handling, which allows the use in clinical and home environments, due to the primary battery built into the system and no need for an external controller, reducing the cost of the device;

Does not need an external controller, whether connected to the mains or some rechargeable battery system;

The device of the present invention can be made in sizes according to the area of the wound, the shape of the bandage being unrestricted;

The device of the present invention is portable, presenting easy application and handling, enabling use in the home or clinical environment;

The device of the present invention is disposable and for single use;

The device of the present invention is self-adhesive;

The device of the present invention comprises structure and layers made of biocompatible materials without restriction;

The device of the present invention can be sterilized;

The device of the present invention uses flexible primary ultra-thin batteries, the number of batteries being unrestricted.

The device of the present invention is flexible, guaranteeing comfort, conforming to the injury and fixation to the user.

Having described an example of a preferred embodiment of the present invention, it should be understood that the scope of the present invention covers other possible variations of the described inventive concept, being limited only by the content of the appended claims, including the possible equivalents therein.

The invention claimed is:

1. An electronic device applied as a bandage in phototherapy, said device comprising:
    a biocompatible adhesive structure formed by a flexible microporous tape;
    a miniaturized flexible electrical circuit comprising a flexible light emitting unit, said light emitting unit comprising an arrangement of LEDs or OLEDs connected to a primary flexible battery that uses voltage ranging from 1 to 5 V and current ranging from 10 to 500 mA, wherein said flexible circuit further comprises electrical contacts with a spring between said electrical contacts, and a dielectric strip in at least one of the electrical contacts; wherein
    said spring is adapted to close the electrical circuit and supply energy to the light-emitting unit after removal of a dielectric strip in one of the miniaturized flexible electrical circuit contacts; and
    a timer controller;
    wherein the flexible light-emitting unit emits wavelengths in the red range between 530 to 700 nm and infrared between 700 nm to 910 nm;
    wherein the device is configured so that at least a portion of the device is overlaid on a target area in a patient; and said portion is able to conform to a surface area of the target area; and
    wherein said portion is flexible, disposable, and for single use.

2. The device according to claim 1 comprising one or two electrical circuits, depending on the application, number, and types of the LEDs.

3. The device—according to claim 1, wherein the LED arrangement—is in series and/or in parallel.

4. The device—according to claim 1, wherein the activation of the LED arrangement—is separate or simultaneous depending on the therapeutic application.

5. The device according to claim 1, wherein the light emitting unit emits light continuously.

6. The device—according to claim 1, wherein the light emitting unit emits light in a pulsed manner.

7. The device—according to claim 1, wherein the device is flexible and self-applied in flexible phototherapy.

8. The device according to claim 1, wherein the device is self-adhesive.

9. The device according to claim 1, wherein the device is constructed for a single use.

10. A method for photobiomodulation of biological tissues by applying the device of claim 1 to a patient in need thereof as a bandage in several different applications.

11. A method for photobiomodulation of biological tissues comprising applying the device of claim 1 to a patient in need thereof in a domestic or a clinical application.

12. A method for healing wounds comprising applying the device of claim 1 to a patient in need thereof.

13. A method of for treating inflammation, edema, and pain comprising applying the device of claim 1 to a patient in need thereof.

\* \* \* \* \*